US006962972B2

(12) United States Patent
Gregoriadis

(10) Patent No.: US 6,962,972 B2
(45) Date of Patent: Nov. 8, 2005

(54) DERIVATIZATION OF PROTEINS

(75) Inventor: Gregory Gregoriadis, London (GB)

(73) Assignee: Lipoxen Technologies Limited (GB)

( * ) Notice: Subject to any disclaimer, the term of this patent is extended or adjusted under 35 U.S.C. 154(b) by 1 day.

(21) Appl. No.: 10/276,552

(22) PCT Filed: May 14, 2001

(86) PCT No.: PCT/GB01/02115

§ 371 (c)(1),
(2), (4) Date: Nov. 18, 2002

(87) PCT Pub. No.: WO01/87922

PCT Pub. Date: Nov. 22, 2001

(65) Prior Publication Data

US 2003/0129159 A1 Jul. 10, 2003

(30) Foreign Application Priority Data

May 16, 2000 (EP) .......................... 00304108

(51) Int. Cl.⁷ ............................ C07K 1/107
(52) U.S. Cl. .................... 530/345; 530/333; 530/300
(58) Field of Search .................. 514/58, 2, 8; 530/300, 530/333, 345

(56) References Cited

U.S. PATENT DOCUMENTS

| | | | |
|---|---|---|---|
| 4,356,170 A | | 10/1982 | Jennings et al. |
| 4,727,136 A | | 2/1988 | Jennings et al. |
| 5,738,846 A | * | 4/1998 | Greenwald et al. ......... 424/85.7 |
| 5,846,951 A | * | 12/1998 | Gregoriadis ................. 514/54 |
| 5,951,974 A | * | 9/1999 | Gilbert et al. ............. 424/85.7 |
| 6,042,822 A | | 3/2000 | Gilbert |

FOREIGN PATENT DOCUMENTS

| | | | | |
|---|---|---|---|---|
| WO | WO92/22331 A | 12/1992 | ..................... | 514/2 |
| WO | WO96/39488 A | 12/1996 | ................. | 435/346 |

OTHER PUBLICATIONS

L Visser & ER Blout. Elastase. II. Optical Properties and the Effects of Sodium Dodecyl Sulfate. 1971, Biochemistry, 10(5), 743–752.*

NJ Turro, X–G Lei, KP Anathapadmanabhan & M Aronson. Spectroscopic Probe Analysis of Protein–Surfactant Interactions: The BSA/SDS System. 1995, Langmuir, 11, 2525–2533.*

M Mammen, S–K Choi & GM Whitesides. Polyvalent Interactions in Biological Systems: Implications for Design and Use of Multivalent Ligands and Inhibitors. 1998, Angewandte Chemie, 37, 2754–2794.*

Z Bradic & RG Wilkins. The Interaction of Hemerytrhrin with Sodium Dodecyl Sulfate and the Release of Iron from the Product with Desferrioxamine B. 1985, Biochmica et Biophysica Acta, 828, 86–94.*

Roy, R., et al "Michael addition of Poly–L–Lysine to N–acryloylated sialosides. synthers is of Influenza A virus Haemagglutinin Inhibitor and Group B Meningococcal Polysaccharide Vaccines" J. Chem.Soc., Chem.Comm (1993) 264–265.

Fernandes, A.I., et al., "Synthesis, characterization and properties of Sialylated catalase" Biochim. Biophys. Acta (1996) 1293(1), 90–96, Abstract only.

Prakash, V., et al., "Effect of SDS, acid, alkali, urea and guanidine hydrochloride on the circular dichroism of alpha–globulin of *Sesamum Indicum* L" Int. J. Peptide Protein Res. (1980) 15, 305–313.

Visser, L. "Elastase. II. Optical properties and the effects of SDS" Biochemistry (1971) 10(5), 743–752.

* cited by examiner

*Primary Examiner*—Bruce R. Campell
*Assistant Examiner*—Andrew D. Kosar
(74) *Attorney, Agent, or Firm*—Dickstein, Shapiro, Morin & Oshinsky, LLP.

(57) ABSTRACT

Proteins are derivitized by reaction of pendant groups, usually groups which are side chains in non-terminal amino acyl units of the protein, in aqueous reactions in the presence of a denaturant. The denaturant is preferably an amphiphilic compound, most preferably an anionic amphiphilic compound such as a long chain alkyl sulphate mono ester, preferably an alkaline metal salt, for instance sodium dodecyl sulphate. The degree of derivatization is increased, while the protein retains activity, such as enzyme activity. The increase in the degree of derivatization enhances the increase in circulation time in vivo and stability on storage and in vivo.

Preferably the derivatizing reagent is an aldehyde compound which reacts with primary amine groups, generally the epsilon-amino group of lysyl units. Derivatization is conducted under reducing conditions to generate a secondary amine derivative.

18 Claims, 4 Drawing Sheets

DERIVATIZATION OF PROTEINS

BACKGROUND OF THE INVENTION

The present invention relates to methods for derivatising proteins, in which a denaturant is included in the reaction mixture, to achieve high degrees of substitution. The method is of particular applicability to derivatisation methods involving reaction of an aldehyde reagent with epsilon amino groups of non-terminal lysyl units of proteins. Novel derivatised protein compounds have high degrees of substitution of polysialic acid chains.

In our earlier application number WO-A-92/22331 we describe methods in which polysaccharides, especially polysialic acids, are used to derivatise drug delivery systems or proteins to increase the circulation time, decrease the immunogenicity and/or increase the stability in vivo of the substrates. There is no worked example of a derivatisation reaction with any protein. Roy et al in J. Chem. Soc. Chem. Comm. 1993, 264–265 describe derivatisation by Michael addition to primary amine groups on proteins of an acrylic-functional sialic acid. The reaction is carried out in the presence of ammonium bicarbonate, which is not generally described as a denaturant.

It is well known that sodium dodecyl sulphate, at the concentration of 0.01M, has an effect on the three dimensional conformation of proteins in aqueous compositions. For instance, Prakash et al in Int. J. Peptide Protein Res. (1980) 15, 305–313, show using circular dichroic spectra that SDS induces more α helical structure in the α-globulin of Sesamum indicum L (a sesame seed). Visser et al, in Biochemistry (1971) 10(5) 743–752 use various optical characteristics of elastase, and other enzymes to determine changes in conformation in the presence of SDS. The protein concentrations in the solutions varied from 0.01 to 0.1%, whilst the SDS concentration was in the range 0.2 to 2% by weight. SDS was shown to inhibit irreversibly the activity of several enzymes under these conditions.

It is known to reduce disulphide bridges between two cysteine units of a protein in the presence of urea which facilitates unfolding of the protein and increase the accessibility of the disulphide groups to mercaptoethanol reducing agent.

As far as the present inventor is aware, anionic amphiphilic compounds, such as SDS, have not been used to affect the conformation of proteins in solution during aqueous derivatisation procedures.

DESCRIPTION OF THE INVENTION

According to the present invention there is provided a new method in which a protein having at least two derivatisable pendant groups (being side chains of amino acyl units) is reacted with a derivatising reagent in aqueous solution to provide a protein derivative, and is characterised in that the derivatisation reaction is carried out in the presence of an effective denaturing concentration of a denaturant. Preferably the degree of substitution of the product at said pendant groups is at least two equivalent groups per mole of protein.

In the method there is usually a subsequent step in which protein derivative is isolated from the denaturant, preferably by a method including a dialysis step.

In the invention, the denaturant may be a chaotropic ion, such as I$^-$ or SCN$^-$, a large anion derived from a strong acid, such as ClO$_4^-$ or CCl$_3$COO$^-$, an organic solvent, urea or a derivative such as a guanidine compound. Preferably it is an amphiphilic compound, more preferably an anionic amphiphile. The anionic amphiphile is preferably a sulphate mono ester of an alcohol having 8 to 24 carbon atoms. Preferably it is added to the reaction mixture in the form of an alkali metal salt. Preferably the amphiphile is a sodium or potassium C$_{8-24}$ alkyl sulphate, most preferably sodium dodecyl sulphate.

In the invention the amphiphile is generally present at a concentration in the range 0.0001 to 0.01M, most preferably in the range 0.0005 to 0.005M, most preferably about 0.001M.

In the invention, the starting protein has at least 2, more preferably at least 5, for instance 10 or more derivatisable groups, all of the same nature. The groups may be hydroxyl groups, thiol groups, carboxylic acid groups or, preferably primary amine groups. Most preferably the derivatisable groups are side chains of lysyl units. Preferably the protein, therefore, has at least 2, more preferably at least 5, for instance 10 or more lysine units in the backbone. Preferably at least 2 reactive groups are derivatised more preferably at least 5 reactive groups are derivatised, that is the degree of derivatisation of the protein is at least 5.

In the invention, the derivatising reagent is a compound having a reactive group suitable for reacting with protein in aqueous solution, optionally in the presence of coupling compounds. Coupling compounds and activation chemistries are described in, for instance, Methods in Enzymology at 135B (Immobilised Enzymes and Cells), 1987, Mosbach ed, Academic Press Inc., New York and in Nucci, M. L. et al. Adv. Drug Delivery Reviews 6, 133–151 (1991).

The reagent is, for instance, a compound used to confer stability, reduce immunogenicity or increase circulation time or solubility of a protein, or to target the protein. It may be an oligomeric or polymeric compound, such as an oligo- or polysaccharide, poly (hydroxyalkyl(alk)acrylamide or -(alk)acrylates), polyvinyl alcohol or polyalkylene glycol, eg polyethylene glycol.

The derivatising reagent may, for instance, be an activated polyethylene glycol (monofunctional), such as tresyl-PEG described in WO-A-9004606 or a succinimidyl succinate ester of PEG. These compounds may react with hydroxyl and thiol groups as well as amine groups.

The present invention is of particular utility where the derivatising reagent to be reacted with primary amine pendant groups is an aldehyde compound. In this case, condensation of the protein with the reagent under reducing conditions produces a secondary amine-linked product.

Most preferably the aldehyde compound is a derivative of a saccharide or polysaccharide, for instance produced by the controlled oxidation of an alcohol. Most preferably the aldehyde is generated in a preliminary step which may be a first step in the process of the invention, in which a saccharide or polysaccharide is reacted under controlled oxidation conditions, for instance using sodium periodate, in aqueous reaction. Most preferably the saccharide or polysaccharide is sialic acid, or a derivative thereof, most preferably a polysaccharide having a terminal sialic acid group, and most preferably is a polysialic acid, that is a polysaccharide comprising at least 5 sialic acid units joined to one another through 2→8 or 2→9 linkages. A suitable polysialic acid has a weight average molecular weight in the range 2 to 2000 kDa, preferably in the range 5 to 50 kDa. Most preferably the polysialic acid is derived from a bacterial source, for instante being, or being derived from, polysaccharide B of E. coli K1, N. meningitidis, Moraxella liquefaciens or Pasteurella aeruginosa or K92 polysaccharide of *E. coli* K92 strain. It is most preferably colominic acid from *E. coli* K1.

It is believed that proteins having at least 5 pendant polysialic acid chains are new. According to a further aspect of the invention there is provided a new protein having at least 5 pendant polysialic acid chains, each having at least 5 sialic acid units joined to one another.

A sialic acid reagent is, for instance, reacted with sodium periodate under controlled oxidation conditions to form a terminal aldehyde at the $C_7$ atom. The oxidation conditions preferably involve sodium periodate at a concentration of around 0.1M, being used in excess to derivatise a solution of polysialic acid. Reaction conditions preferably involve reaction at room temperature for 5 to 60 minutes. In order to deactivate excess periodate, conventional means such as reaction with ethylene glycol, are used.

The derivatisation step of the method of the invention is preferably carried out with the protein in the aqueous reaction mixture at a temperature in the range 0 to 60° C., preferably 10 to 45° C., for instance at a raised temperature in the range 30 to 40° C. The protein is preferably present at a concentration in the range 0.1 to 100 g/l, preferably in the range 1 to 20 g/l. The reaction mixture may contain other ingredients such as dissolved inorganic salts, for instance to buffer the solution of a suitable pH.

The protein which is derivatised in the invention may be, for instance, a therapeutically active compound. The derivatisation reaction may, for instance, be for controlling the hydro- or lipo-philicity of the protein, for instance to adjust its solubility in liquid media, especially to increase its hydrophilicity and solubility in aqueous media. The derivatisation reaction may be, as in our earlier publication WO-A-92/22331, for increasing the circulation time, decreasing the immunogenicity and/or increasing the stability on storage, in vitro or in vivo, of a therapeutic compound. Derivatisation with poly(ethylene glycol) increases hydrophilicity of the protein, which may increase aqueous solubility or availability, increase circulation time or decrease the immunogenicity of the protein. The presence of the denaturant compound increases the degree of derivatisation, thereby enhancing the improvement in solubility, circulation time and/or immunogenicity or the increase in stability of the protein. It has been found that this increase in degree of derivatisation may be carried out without adversely affecting the activity of the protein, for instance its enzyme activity. Thus, in contrast to the findings of Visser et al (op. cit.) the presence of the anionic amphiphile does not irreversibly deactivate the protein, indeed, as shown below, it inhibits deactivation. The derivatisation may alternatively be for providing active or passive targeting by attachment of polymers or binding ligands.

Pharmaceutically active proteins whose availability in the circulation would be beneficially prolonged by the invention are cytokines, such as interleukins, for instance IL-2, IL-6 or IL-1, interferons, tumour necrosis factor (TNF), growth factors, peptide hormones, such as insulin, as well as enzymes for instance for use in enzyme therapy, as well as immuno-globulins, and aprotinin.

Alternatively the protein may be a carrier or adjuvant and the derivatising reaction conjugates pharmaceutically active, or diagnostically useful ligands to the protein to optimise the delivery of the useful ligand to a target issue.

EXAMPLES

In the following examples, catalase is used as a model protein.

General Methods

Catalase Determination

Catalase is a tetrameric haemprotein that catalyses the degradation of hydrogen peroxide to oxygen and water. The reaction can be used to determine enzyme activity. The reaction is a first order reaction, whereby the amount of peroxide substrate decomposed is directly proportional to the concentration of both substrate and enzyme. Provided the concentration of substrate is constant between experiments, any difference in decomposition rate will therefore be a function of enzyme activity present. In the present examples, the drop in absorbance hydrogen peroxide at 240 $\mu$m from 0.450 to 0.400, corresponding to the decomposition of 3.45 $\mu$ moles of hydrogen peroxide in a cuvette having a reaction volume of 3 ml, is determined.

Concentration of catalase (active and inactive) relies upon the fact that the enzyme exhibits a characteristic absorption maximum, the Soret band at 405 nm. Catalase concentration is determined spectrophotometrically.

Catalase, Insulin, Aprotinin and IgG Labelling and Clearance Determination

Catalase, insulin, IgG and aprotinin were radiolabelled using the conventional methods using $^{125}I$, usually the chloramine-T method.

Radiolabelled protein in the circulation was determined using techniques described in Fernandes, A. I. et al, Biochem. Biophys. Acta (1997) 1341, 26–34.

Activation of Colominic Acid (Polysialic Acid)

Colominic Acid is a derivative of *E. coli* K1, having an average molecular weight of around 10 kDa. The polysaccharide consists substantially only of 2–8 linked sialic acid units.

Figure 1:
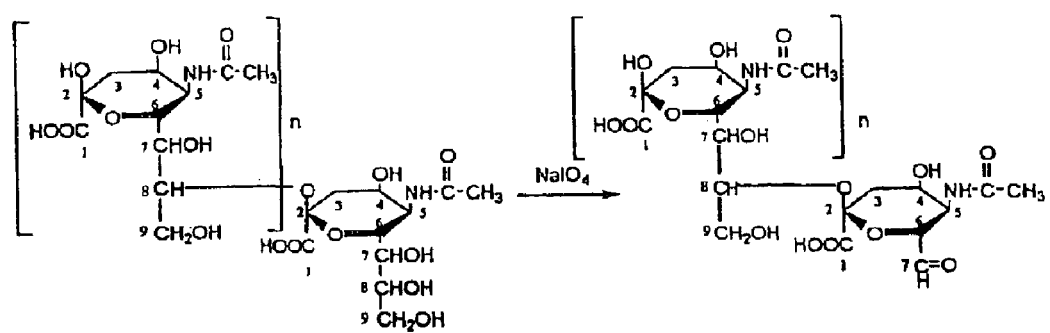
FIG. 1 is a reaction scheme for the derivatisation of polysialic acid.

The activation of (oxidation) colominic acid is carried out as follows. A 0.1M aqueous solution of sodium periodate is formed. 1 ml of the sodium periodate solution is mixed with 10 mg colominic acid in the dark, and the reaction mixture stirred for 15 minutes at room temperature and pressure (around 20° C., 1 bar). The reaction is terminated by addition of 2 ml ethyleneglycol, followed by stirring for 30 minutes under the same conditions. Subsequently the mixture is extensively dialysed at 40° C. against a 0.01% by weight ammonium carbonate buffer. The dialysate is freeze-dried overnight, then refrigerated until further use. The reaction scheme is shown in FIG. 1.

Determination of Sialic Acid

Sialic acid is determined by forming a 0.5 ml sample (having a concentration in the range 4 to 40 mg/ml sialic acid) in aqueous solution, added to this 0.5 ml resorcinol reagent. The mixture is boiled in a water bath for 30 minutes in sealed tubes. The mixture is cooled for 20–30 minutes and its absorbance read at 570 nm against control mixtures of appropriate buffer (i.e. of the type and concentration in which the original sample is presented) and reagent.

Determination of Poly(ethylene glycol)

The level of pegylation was estimated by the assay of PEG using ammonium ferrithiocyanate (A. Nag, G. Micra and C Ghost, Anal. Biochem. 237:224–231, 1996).

Determination of Protein

Samples containing derivatised IgG, aprotinin or insulin were assessed for soluble protein content using the Bradford method. 100 μl protein solution (having a protein concentration in the range 10 to 100 μg/ml) and 1 ml colour reagent (acid/dye solution) were mixed. The absorbance is read at 595 mm against a suitable blank.

The IgG used in the following examples was tested for its sialic acid content using this method. It was found to have 2% sialic acid content. This figure is taken into account when assessing the level of polysialylation using colominic acid derivatisation according to the examples.

Reagents

The catalase was obtained from the Sigma company. Insulin is obtained from Sigma IgG is bovine serum IgG obtained from Sigma. A protnin was obtained from BDH. Monomethoxy polyethylene glycol succinimidyl succinate (molecular weight about 5 kD) was obtained from Sigma. Colominic acid was obtained from Sigma. Sodium dodecyl sulphate was obtained from Sigma. Urea was obtained from BDH.

Example 1

Reaction of Catalase with Colominic Acid

The present example illustrates the effect of reaction time in the activated colominic acid—catalase derivatisation reaction, by assessing the catalase activity after recovery of the derivatised enzyme.

The derivatisation was carried out using 24 mg of catalase with 50 mg of activated colominic acid, in the presence of 20 mg sodium cyanoborohydride in 5 ml potassium hydrogen phosphate buffer. The reactants are stirred for a period up to 48 hours at 35 to 40° C. For a derivatisation reaction carried out in the presence of SDS, solid SDS is dissolved in the phosphate buffer to provide a final concentration of $1 \times 10^{-3}$M SDS.

After reaction times of zero hours (i.e. as quickly as possible after the reaction mixture is made up), 6 hours, 12 hours, 24 hours and 48 hours, the reaction is stopped by addition of 70% ammonium sulphate solution to precipitate out protein. The precipitated mixture is cooled on ice and stirred for one hour, then centrifuged at 3500 rpm for 45 minutes. The supernatant is discarded and the pellet washed with saturated ammonium sulphate solution, spun again for ten minutes at the same speed, and the supernatant discarded. The pellet is redissolved in 5 ml phosphate buffered saline. The resultant solution is dialysed extensively at −4° C. against four changes of phosphate buffered saline. The solution is then passed down a Sephadex (trade mark) G-100 column and peaks collected and assayed for catalase and colominic acid content.

Figure 2:
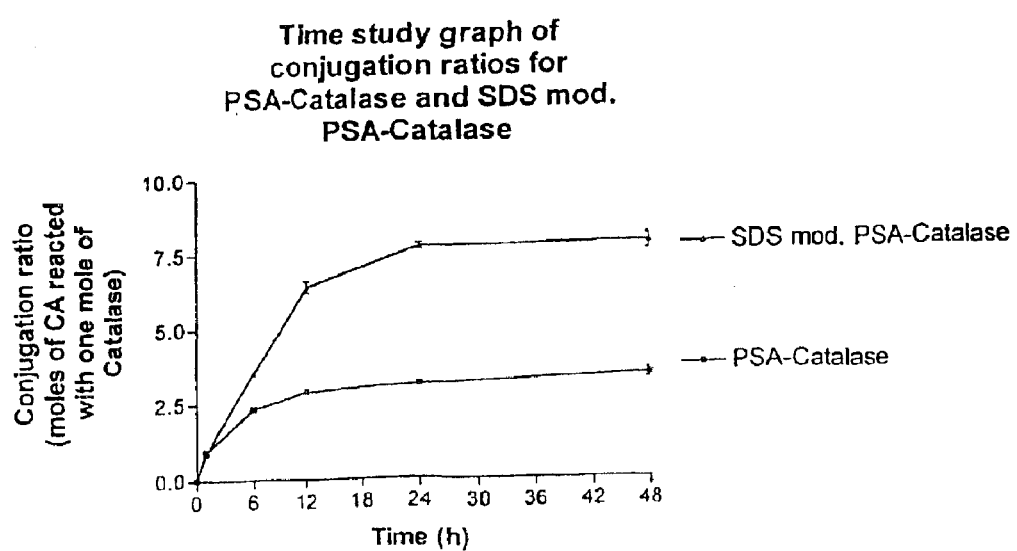
FIG. 2 shows results of Example 1.

FIG. 2 indicates the conjugation ratio (degree of substitution) of colominic acid with catalase in the presence and absence of SDS. The results show that the presence of SDS increases the maximum conjugation ratio by a factor of about 3. The maximum level of derivatisation in the presence of SDS appears to be around 8 moles colominic acid per mole catalase.

Figure 3:
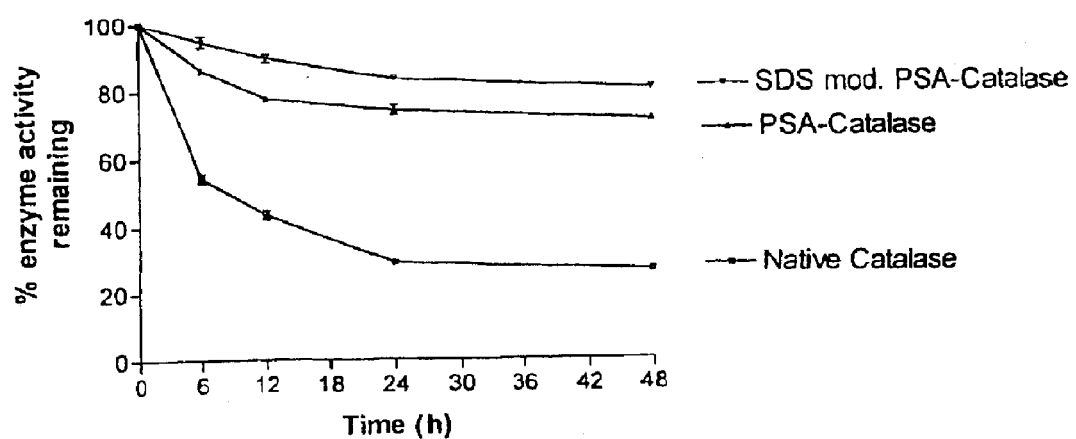
FIG. 3 shows results of Example 1.

The derivatised catalase compounds were also tested against native catalase for their enzyme activity. The results are shown in FIG. 3. The results for catalase alone in FIG. 3 show the effect of subjecting catalase to the reaction conditions but without the addition of activated colominic acid. This shows that catalase activity is lost under those conditions, but that the loss of activity is inhibited by polysialylation. The inhibitor is greater when the polysialylation takes place in the presence of SDS.

Example 2

Determination of Effect of Changing SDS Concentration on Catalase Activity

The general coupling procedure used in experiment 1 was used to derivatise catalase, except that the SDS concentration was used at 0.01% by weight, 0.02% by weight and 0.029% by weight ($1 \times 10^{-3}$M), with the derivatisation reaction being continued for a period of 48 hours.

The derivatised catalase products were assessed for their catalase activity using the general test described above. The times taken for the enzymes to reduce the absorbance from 0.45 to 0.40 are shown in table 1 as compared to native catalase.

TABLE 1

| Concentration SDS (%) | Time for Δ Ab (min) |
|---|---|
| 0 | 4 |
| 0.01 | 13 |
| 0.02 | 21 |
| 0.029 | 44 |

Example 3

Native catalase, catalase derivitised using $1 \times 10^{-3}$M SDS, for a reaction period of 48 hours, and catalase derivatised using the same reaction time but in the absence of SDS, were compared at different concentrations of hydrogen peroxide to form Hanes Woolf plot. The Km (substrate concentration at which the reaction rate is half of its maximal value) for native catalase is 83.95 mM, for the colominic acid-catalase generated in the absence of SDS, Km is 114.4 mM, and for catalase modified in the presence of SDS, the Km is 140.8 mM.

Example 4

Polysialylation of Proteins in the Presence and Absence of SDS

For each protein, 1 mg of $^{125}$I-labelled and unlabelled protein is reacted with 83.3 mg activated colominic acid in the presence of 20 mg sodium borohydride in 5 ml potassium hydrogen phosphate. For reactions in the presence of SDS, SDS is dissolved to form a final concentration of $1 \times 10^{-3}$M. The derivatisation reaction is carried out for 48 hours at a temperature in the range 35 to 40° C.

After the reaction, the derivatised protein is recovered using the same general technique as in example 1, but using centrifugation at 9000 rpm. The column used for isolation is Sephadex G-50.

Table 2 shows the conjugation yields, that is the degree of derivatisation, with and without SDS, for the four proteins.

Aprotinin has 4 lysyl units having derivatisable amine groups and 2 terminal amino groups available for derivatisation by aldehyde reagents.

TABLE 2

| Formulation | Protein-PSA Conjugation Yield Protein:PSA (mole) | (SDS) Modified Protein-PSA Conjugation Yield Protein:PSA (mole) |
|---|---|---|
| IgG | 1:4.25 | 1:12.37 |
| CATALASE | 1:3.76 | 1:8.37 |
| APROTININ | 1:1.50 | 1:5.59 |
| INSULIN | 1:1.90 | 1:6.55 |

The results indicate that, for each of the proteins tested, the presence of SDS increases the degree of derivatisation.

Example 5B

In vivo Clearance Rates

The labelled insulin, aprotinin and IgG, in their native forms, and derivatised with colominic acid (polysialic acid PSA) in the presence and absence of SDS are administered to mice to determine the rate of clearance from the circulation. The in vivo tests are carried out using the general technique described in example 1 of WO-A-92/22331, by injection of protein or derivatised protein in the dose shown in table 3. The animals were bled from the tail vein immediately before and, immediately after, at 30 minutes, 1 hour, 4 hours, 6 hours, 12 hours, 24 and 48 hours after injection to determine the level of $^{125}$I label remaining in the circulation. From the logarithmic curve of percent initial radioactivity against time following injection, the area under the curve is determined. The results for the various proteins are shown in table 3.

TABLE 3

| Protein | Derivatisation | Dose mg | Area under curve (hg/l) |
|---|---|---|---|
| Insulin | Native Ins | 0.400 | 0.7 |
| | PSA:Ins | 0.3960 | 2.3 |
| | SDS/PSA:Ins | 0.6640 | 6.4 |
| Aprotinin | Native Apn | 0.670 | 1.6 |
| | PSA:Apn | 0.620 | 3.0 |
| | SDS/PSA:Apn | 0.770 | 6.6 |
| IgG | Native IgG | 0.720 | 46 |
| | PSA:IgG | 0.734 | 60 |
| | SDS/PSA:IgG | 0.726 | 75 |

The results in Table 3 show that derivatisation of each protein with colominic acid results in an increase in the circulation time, thereby confirming the results indicated in WO-A-92/22331. The degree of increase in circulation time is significantly increased where derivatisation is conducted in the presence of SDS.

Example 6

Derivatisation in the Presence of Urea

The derivatisation method according to Example 1 was repeated using IgG in place of catalase. 5M urea or 1×10$^{-3}$M SDS were used. The reaction in individual aliquots of reaction mixture was stopped after 6, 12, 24 and 48 hours. The degree of derivatisation was determined after assessing the level of protein using the Bradford technique described above and the level of sialic acid using the resorcinol method described above. The results are shown in FIG. 4.

Figure 4:
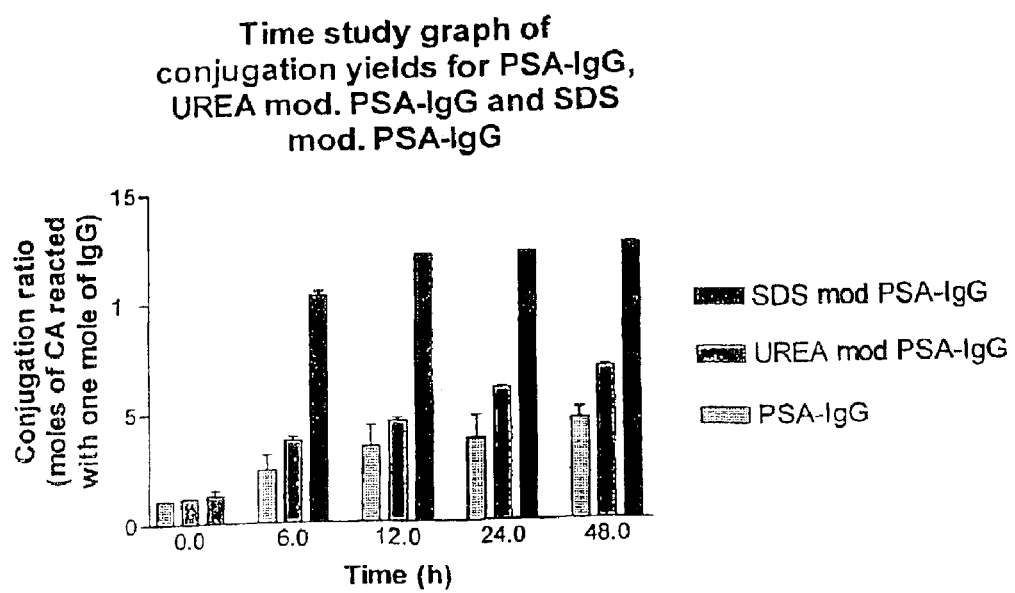
FIG. 4 shows the results of Example 6.

The results in FIG. 4 show that the presence of urea increases the level of derivatisation, though by a lesser amount than SDS, at concentrations normally expected to provide an alteration in protein conformation.

Example 7

Pegylation and Polysialylation of IgG in the Presence of SDS

IgG, as used in the above examples was subjected to derivatisation with oxidised colominic acid (CA) in the absence and presence of 10$^{-3}$M SDS under the general conditions used in Example 4.

The same protein was also derivatised by monomethoxy poly(ethlene glycol) succinimidyl succinate (ssPEG) in the absence of SDS and in the presence of 10$^{-3}$M SDS. The reaction is based on Tsutsumi et al (1995) Brit. J. Cancer 71:963–968. IgG in 0.2M phosphate buffer, pH 7.2, was allowed to react with a 50-fold molar excess of methoxy-polyethylene glycol succinimidyl succinate (ss-PEG) at room temperature for 10 min. The reaction was stopped by addition of 5-fold molar excess ε-amino caproic acid over ss-PEG. The resulting PEG-IgG was purified and separated by gel permeation chromatography (SG-100; 0.2M phosphate buffer). For the reaction in the presence of SDS, the IgG was first contacted with 10$^{-3}$M SDS in the 0.2M phosphate buffer at raised temperature for 12 hours. Otherwise the reaction and recovery was the same.

The degree of derivatisation of pegylated and polysialyated IgG=s was determined using the methods described above. The results are shown in table 4.

TABLE 4

| | Degree of derivatisation Protein: (PEG or CA) mole | |
|---|---|---|
| Regent | Without SDS | With SDS |
| CA | 1:3.1 | 1:8.5 |
| SsPEG | 1:12.2 | 1:18.6 |

The presence of SDS increases the level of derivatisation for a PEG reagent as well as for a polysialic acid reagent. The PEG reagent gives a higher degree of substitution than the colominic acid reagent.

What is claimed is:

1. A method for producing a protein derivative in which a protein having at least two identical derivatisable pendant groups, which are selected from the group consisting of hydroxyl, thiol, carboxylic acid and amine groups on side chains of amino acyl units, is reacted with a derivatising reagent which is a polysialic acid and wherein the polysialic acid reacts with at least one of said identical derivatisable groups in aqueous solution to provide the protein derivative, and wherein the derivatisation reaction is carried out in the presence of an effective denaturing concentration of a denaturant.

2. The method according to claim 1 in which the denaturant is an amphiphilic compound.

3. The method according to claim 2 in which the amphiphilic compound is anionic.

4. The method according to claim 3 in which the denaturant is a $C_{8-24}$ alkyl sulphate monoester.

5. The method according to claim 1 in which the denaturant is present at a concentration in the range 0.0001–0.01M.

6. The method according to claim 1 in which the protein derivative is isolated from the denaturant.

7. The method according to claim 1 in which the protein has at least 5 derivatisable groups.

8. The method according to claim 1 in which the protein is a therapeutically active compound.

9. The method according to claim 1 in which the degree of substitution of the product is at least 2, whereby each mole of protein derivative has at least two equivalents of derivatised pendent side residues.

10. A protein compound having at least 5 pendant polysialic acid chains, each having at least 5 sialic acid units joined to one another, in which the polysialic acid chains are joined to side-chains of non-terminal lysyl units.

11. The protein compound according to claim 10 in which the polysialic acid chains are joined to said side-chains of non-terminal lysyl units through secondary amine linkages.

12. The protein compound according to claim 10 in which the polysialic acid chains each have at least 10 mutually linked sialic acid units.

13. The method according to claim 4 in which the denaturant is sodium dodecyl sulphate.

14. The method according to claim 6 in which the protein derivative is isolated by dialysis.

15. The method according to claim 1 in which the derivatisable pendant groups are epsilon amino groups of lysyl units.

16. The method according to claim 1 in which the derivatising reagent is an aldehyde derivative of the polysialic acid.

17. The method according to claim 9 in which the degree of substitution of the product is at least 5.

18. The protein compound according to claim 12 in which the polysialic acid chains have 20 to 50 mutually linked sialic acid units.

* * * * *